(12) United States Patent
Kim et al.

(10) Patent No.: US 8,367,373 B2
(45) Date of Patent: Feb. 5, 2013

(54) OVIDUCT SPECIFIC EXPRESSION PROMOTER AND RECOMBINANT EXPRESSION VECTOR COMPRISING THE SAME

(75) Inventors: Tae Yoon Kim, Seoul (KR); Sang Hoon Kim, Seoul (KR); Ik Soo Jeon, Gyeonggi-do (KR); Sung Jun Byun, Gyeonggi-do (KR); Dong Heon Shin, Seoul (KR); Nam Soo Kim, Seoul (KR)

(73) Assignee: Industry-Academic Cooperation Foundation, The Catholic University of Korea, Seoul (KR)

( * ) Notice: Subject to any disclaimer, the term of this patent is extended or adjusted under 35 U.S.C. 154(b) by 635 days.

(21) Appl. No.: 12/514,730

(22) PCT Filed: Nov. 15, 2007

(86) PCT No.: PCT/KR2007/005737
§ 371 (c)(1),
(2), (4) Date: Mar. 12, 2010

(87) PCT Pub. No.: WO2008/060110
PCT Pub. Date: May 22, 2008

(65) Prior Publication Data
US 2010/0167343 A1    Jul. 1, 2010

(30) Foreign Application Priority Data
Nov. 16, 2006  (KR) .......................... 10-2006-0113141

(51) Int. Cl.
*C12P 21/02* (2006.01)

(52) U.S. Cl. ..................... 435/69.1; 435/367; 435/320.1; 536/24.1

(58) Field of Classification Search ........................ None
See application file for complete search history.

(56) References Cited

U.S. PATENT DOCUMENTS
2004/0172666 A1    9/2004  Iijima

OTHER PUBLICATIONS

International Search Report, PCT/KR2007/005737, Apr. 2007.
Kim et al, Expression of AGR-2 in Chicken Oviduct During Laying Period, Journal of Biochemistry and Molecular Biology, vol. 40, No. 2, Mar. 2007, pp. 212-217.
Gao et al, Expression and Preliminary Characterization of Recombinant Human Tissue Kallikrein in Egg White of Laying Hens, Poultry Science, vol. 85(7), Jul. 2006, pp. 1239-1244.
Zhang et al, AGR2, An Androgen-Inducible Secretory Protein Overexpressed in Prostate Cancer, Genes, Chromosomes and Cancer, vol. 43(3), Jul. 2005, pp. 249-259.
Shih et al, Characterization of the AGR2 Gene, a Homologue of *X. laevis* Anterior Gradient 2, From the Zebrafish, Danio Rerio, Gene Expression Patterns, vol. 7(4), Feb. 2007, pp. 452-460.

*Primary Examiner* — Jim Ketter
(74) *Attorney, Agent, or Firm* — Merchant & Gould

(57) ABSTRACT

An oviduct specific expression promoter and a recombinant expression vector including the same. A promoter of an AGR2 gene is expressed specifically in the chicken oviduct, and a recombinant expression vector includes the promoter and a desired gene for encoding a desired protein. The oviduct specific promoter and the recombinant expression vector including the promoter can induce the expression of a protein specifically in the oviduct, i.e., an organ that secrets proteins so as to accumulate with a large amount in the egg. Accordingly, the oviduct specific promoter and the recombinant expression vector of the present invention can be advantageously used to produce transformed chickens, which can massively yield useful elements of high added value, produce functional eggs, and improve the economic traits of the poultry.

15 Claims, 6 Drawing Sheets

OVIDUCT SPECIFIC EXPRESSION PROMOTER AND RECOMBINANT EXPRESSION VECTOR COMPRISING THE SAME

TECHNICAL FIELD

The present invention relates to an oviduct specific expression promoter and a recombinant expression vector including the same. More particularly, the present invention relates to a promoter of an anterior gradient 2 (AGR2) gene, which is expressed specifically in the chicken oviduct, and a recombinant expression vector including the promoter and a desired gene for encoding a desired protein.

BACKGROUND ART

The chicken oviduct also referred to as a "Fallopian tube" is an organ for secreting several proteins, such as ovalbumin, in which proliferation and differentiation of cells occur periodically. In particular, it is reported that the oviduct wall of an ovipara secretes nutritive elements and an eggshell to feed to an egg, and the oviduct of a chicken secretes protein to accumulate with a large amount in the egg (*Modern Poultry Science*, Bong-Kug OHH, 1988).

In general, an egg is a food abundant of nutritive elements such as proteins, vitamin A, cholesterol and inorganic matters, and has excellent nutritive values with the protein content about twice of that of milk and the fat content higher than those of milk, cheese and beef. It is also reported that the egg has functional properties such as immunologic enhancement and remedial value. Particularly, it is reported that the white of the egg acts as an antidote when a toxic substance and/or an irritant substance is taken in and also protects the gastric and intestinal mucosa, thereby preventing the same from an ulcer. Accordingly, the consumption of eggs is sharply rising in the recent days, and there is increasing interest on the development of methods of producing functional eggs that contain new functional contents useful for the human body. Of various conventional methods, which have been developed in relation with the foregoing, Korean Patent Application Publication No. 2006-0030186 discloses a method of producing eggs with increased taurine content by breeding layer chickens with a feed to which feather meal and pyridoxine are added. Korean Patent Application Publication No. 2003-0082207 discloses a method of producing mineral-activated salicomia herbacea eggs by adding salicomia herbacea into a general formula feed, by which the eggs include a large amount of minerals, such as Mg, Ca, K, Fe, P, I, Na and salts, which are contained in the sea. Furthermore, Korean Patent No. 0567311 discloses a method of producing special eggs using a layer chicken feed composition, which includes aloe contents. The conventional methods of producing functional eggs are in consideration that specific nutritive elements in the white and the yellow can increase in proportion to the amount of specific elements added to a formula feed for chickens. However, these methods have a drawback in that the incidental expense of the additives increases in addition to the expense of the formula feed.

Accordingly, there are new approaches to produce functional eggs based on the development of genetic engineering. Particularly, of these approaches, studies on a transgenic chicken are on the limelight. That is, various studies are being carried out in many countries in order to develop chickens that lay eggs containing genetic material useful for the human body. Genetic engineering technologies, which have been used to produce the transgenic chicken up to date, include a method of producing the transgenic chicken using a vector, which includes a gene expressing a useful protein (Harvey A. J. et al., Nature Biotechnology, 20: 396-399, 2002) and methods of producing a useful protein in the chicken using a promoter (Harvey A. J. & Ivarie R., Poultry Science 82: 927-930, 2003; Chen Y. X., Mol. Vis. 17: 874-883, 2004). Especially, as the method of using a promoter, some methods using cytomegalovirus (CMV) promoter and/or ovalbumin promoter have been developed. However, since the CMV promoter is randomly expressed in the whole body, expression control is difficult and the CMV promoter may change the physiological phenomena of the chicken. On the contrary, the ovalbumin promoter can be specifically expressed in the chicken oviduct and the egg to tissue-specifically induce the expression of protein, thereby minimizing the abnormal physiological phenomena of the chicken. However, since the ovalbumin promoter is patented by foreigners, even if the transgenic chicken using the ovalbumin promoter is produced, its industrialization is not easy at all. Furthermore, only a minimum number of examples produce a tissue-specific transgenic chicken using the ovalbumin promoter.

Accordingly, it is required to find a novel gene and a promoter, which are tissue-specifically expressed without taking a great effect on the physiological phenomena of chickens, in order to produce functional eggs, transgenic chickens that can lay the functional eggs, and proteins useful to the human body from the transgenic chickens.

The present inventors have studied to find a novel promoter, which induces tissue-specific expression in order to produce functional eggs and transgenic chickens which can lay the functional eggs. As a result, the present inventors found out a promoter region of the AGR2 gene which is oviduct-specifically expressed, and succeeded in producing a recombinant expression vector including the promoter region, thereby completing the present invention.

DISCLOSURE

Technical Problem

Accordingly, the present invention provides a promoter of the AGR2 gene, which is oviduct-specifically expressed.

The present invention also provides a recombinant expression vector including the above-mentioned promoter and a base sequence for encoding a desired protein operably linked to the above-mentioned promoter, and a cell transformed with the recombinant expression vector.

The present invention further also provides a method of producing a desired protein, which includes culturing the above-mentioned transformed cell.

Technical Solution

According to an aspect of the present invention, there is provided an oviduct specific expression promoter including 1996 to 2882 base sequences (−7th to −893rd from the transcription initiation site of the AGR2 gene) of SEQ ID NO: 1.

According to another aspect of the present invention, there is provided a recombinant expression vector including the above-mentioned promoter of the present invention and a base sequence for encoding a desired protein operably linked to the promoter.

According to a further aspect of the present invention, there is provided a cell transformed with the above-mentioned recombinant expression vector of the present invention.

According to a yet another aspect of the present invention, there is provided a method of producing a desired protein, which includes culturing the above-mentioned transformed cell of the present invention.

The present invention will now be described in more detail.

As major features of the present invention, there is found a promoter region of the AGR2 gene which is oviduct-specifically expressed and, accordingly, a recombinant expression vector, which includes the corresponding promoter and a base sequence for encoding a desired protein operably linked to the promoter, is produced.

In order to find proteins, which are oviduct-specifically expressed, the present inventors used the proteome method, which is recently on the limelight owing to advanced technologies and the development of equipment. The proteome method is a technology enabling a number of proteins in a cell or a tissue to be recognized at a glance, by which the function and identification of the proteins produced by genes can be very correctly and easily examined. Accordingly, at first, the present inventors extracted proteins from the oviduct of chickens in different growth stages, such as 5, 35 and 65 week old chickens, carried out the first dimensional electrophoresis, in which the proteins are separated according to the isoelectric point of the proteins, and the second dimensional electrophoresis, in which the proteins are separated according to the molecular weight of the protein, stained the expressed proteins using a staining reagent, and analyzed the expression behavior of the proteins in the oviduct according to the age through image analysis (see Example 1). As a result, since the activity of the oviduct of the 35 week old chicken was strongest, protein expression of the 35 week old oviduct was more significant than those of the other chickens (FIGS. 1, 2 and 3). Eight (8) proteins, which were more strongly expressed in the 35 week old oviduct than in the other chicken oviducts, were selected through the image analysis, and five of the selected proteins were finally identified using a mass spectrometer (see FIG. 4 and Table 1). The identified five proteins include calumenin, also known as calcium binding protein (Genebank Accession No. AAB97725), acidic ribosomal phosphoprotein (ARP), also known as estradiol independent house keeping gene (Genebank Accession No. NP_990318), prohibitin (Genebank Accession No. AAB54971), heart fatty acid binding protein (HFBP; Genebank Accession No. NP_0010260660) and AGR2 (Genebank Accession No. XP_418698); the other three proteins were not identified. Based on the above-mentioned result, the present inventors were able to convince that the identified five proteins were being expressed in the oviduct of the 35 week old chicken at a significantly high value.

In order to see again whether or not the identified five proteins are expressed at a significantly high value only in the oviduct tissue of the 35 week old chicken, the whole RNA was extracted from the oviduct of 5, 35, 55 and 83 week old chickens, and the expression status of the RNA was analyzed using a reverse transcription polymerase chain reaction (RT-PCR) (see Example 3). As a result, the five proteins were rarely expressed in the premature 5 week old oviduct; the RNA of calumenin and the RNA of ARP were expressed from the 35 week old oviduct but only with a small amount. In the case of prohibitin and HFBP, high RNA expression was observed in the 35 and 55 week old oviducts, but the amount of RNA expression decreased in the 83 week old oviduct. On the contrary, the RNA of AGR2 was expressed very highly through the 35, 55 and 83 week old oviducts (see FIG. 5). Even though these results are different from that obtained using the proteome method, the RNA of AGR2 was highly expressed in the 35 week old chicken, which is in the egg-laying period. Accordingly, it was assumed that the AGR2 gene and the promoter of the gene can be utilized as a useful gene to produce functional eggs.

Furthermore, in order to examine that the identified five proteins are being expressed in the chicken oviduct only, the present inventors extracted RNA from tissues other than oviduct, such as the heart, the liver, the kidney and the muscle of a chicken, in addition to the ampulla and the isthmus corresponding to the chicken oviduct. Using primers, which were prepared based on the base sequence of genes encoding the above-identified five proteins, an RT-PCR was performed to comparatively analyze the expression status of the five proteins in the oviduct with respect to that in the other tissues (see Example 4).

As a result, of the identified five proteins, most of four proteins except for calumenin were expressed in the muscle; large amounts of prohibitin, HFPB and AGR2 were expressed only in the muscle and the ampulla of the oviduct. In addition, calumenin and prohibitin were expressed in the isthmus of the oviduct but with a very small amount. On the contrary, it was observed that AGR2 was very strongly expressed in the ampulla and the isthmus of the oviduct (see FIG. 6). Accordingly, it could be understood that AGR2 of the identified five proteins is a protein that is specifically expressed in the muscle and the oviduct tissue.

The oviduct is an organ for secreting a large amount of proteins to store in the egg. In the oviduct, proliferation and differentiation of cells occur periodically. The present inventors, after understanding that the AGR2 protein is specifically expressed in the oviduct, assumed that functional eggs having useful elements accumulated therein can be produced using the promoter region of AGR2 gene only when the promoter region is located. In order to convince the probability of the production of the functional eggs using the promoter region, the present inventors examined the degree of expression of the AGR2 protein in the white of hatching eggs, subjected to egg cultivation or artificial incubation in an egg hatching facility. As a result, it was observed that a large amount of AGR2 protein was expressed in the white of the egg subjected to the cultivation (see FIG. 7). In order to locate a region corresponding to the promoter region of the AGR2 gene, a region corresponding to −893 bp, −1698 bp or −2888 bp upstream of a region, which corresponds to −7 from the transcription initiation site (i.e., A base of ATG) of the AGR2 gene in the chicken genome, was acquired using NCBI database, by performing a PCR, and the base sequence was analyzed (see FIG. 8). Accordingly, the base sequence including −2888 bp, upstream of the region corresponding to −7 from the transcription initiation site of the AGR2 gene, was acquired. The base sequence including the acquired value was indicated with SEQ ID NO: 1, and A base, corresponding to 2889th in the SEQ ID NO: 1, was indicated with +1 as the transcription initiation site.

Accordingly, the present inventors measured luciferase activity in order to examine whether or not some of base sequences including −893 bp, −1698 bp and −2888 bp upstream of a region, which corresponds to −7 from the transcription initiation site of the AGR2 gene, have promoter activity (see Example 7-2). As a result, it was observed that the base sequences, assumed as having the promoter activity, induced the expression of a luciferase gene. In particular, the promoter activity of base sequences −7 to −2888 bp from the transcription initiation site of the AGR2 gene increased about 8 times compared to that of base sequences −7 to −893 bp from the transcription initiation site of the AGR2 gene, and the promoter activity of base sequences −7 to −1698 bp from the transcription initiation site of the AGR2 gene increased about 3.5 times compared to that of base sequences −7 to −893 bp from the transcription initiation site of the AGR2 gene (see FIG. 10). In consideration of the results, it was conceived that base sequences corresponding to −7 to −893 bp, −7 to −1698 bp and −7 to −2888 bp from the transcription initiation site of the AGR2 gene are the promoter regions of the AGR2 protein, which are expressed specifically in the oviduct.

Accordingly, the present invention provides an oviduct specific expression promoter including 1996 to 2882 base sequences ($-7^{th}$ to $-893^{rd}$ from the transcription initiation site of the AGR2 gene) of SEQ ID NO: 1. The promoter may be an oviduct specific expression promoter including 1191 to 2882 base sequences ($-7^{th}$ to $-1698^{th}$ from the transcription initiation site of the AGR2 gene) of SEQ ID NO: 1, or an oviduct specific expression promoter including 1 to 2882 base sequences ($-7^{th}$ to $-2888^{th}$ from the transcription initiation site of the AGR2 gene) of SEQ ID NO: 1.

The promoter of the present invention expresses a protein specifically in the oviduct of a chicken. According to an example of the present invention, it was observed that the AGR2 protein of a chicken was expressed with a very small amount in a muscle tissue but was expressed with a very high efficiency in oviduct tissues of the chicken, such as the ampulla and the isthmus. As mentioned above, the promoter of the present invention induces oviduct specific expression of proteins at a very high efficiency, and thus an expression vector, which causes a desired extraneous protein to be oviduct-specifically expressed, can be produced using the promoter of the present invention.

Accordingly, the present invention provides a recombinant expression vector including an oviduct specific promoter, which has 1996 to 2882 base sequences ($-7^{th}$ to $-893^{rd}$ from the transcription initiation site of the AGR2 gene), and a base sequence for encoding a desired protein operably linked to the promoter.

The term "promoter" generally indicates a gene region including the transcription initiation site, located upstream of an encoding region. The promoter includes a TATA box region for controlling gene expression, a CAAT box region, a region responding to an external stimulus to influence the gene expression, an enhancer for promoting the expression of substantially all genes irrespective of location and direction, and so on.

The term "expression vector" indicates a plasmid, a virus or another medium, known in the art, into which the promoter of the present invention and a base sequence for encoding a desired protein operably linked to the promoter, can be inserted or introduced. The promoter of the present invention and the base sequence for encoding a desired protein operably linked to the promoter can be operably linked to an expression control sequence. The gene sequence and the expression control sequence, which are operably linked to each other, may be included in one expression vector having both a selectable marker and a replication origin. The "operably linked" gene and expression control sequences may be linked to each other in a fashion that a suitable molecule bound to the expression control sequence can enable gene expression. The term "expression control sequence" indicates a DNA sequence that controls the expression of an operably-linked polynucleotide sequence in a predetermined host cell. The control sequence includes a promoter for performing transcription, an operator sequence for controlling transcription, a sequence for encoding a suitable mRNA ribosome binding region, and a sequence for controlling the termination of transcription and decoding.

The expression vector of the present invention can be produced by inserting a promoter of the present invention into a basic skeleton of a typical protein expression vector, and inserting a base sequence for encoding a desirable protein, downstream of the promoter. Hence, available examples of the vector of the present invention may include plasmids, such as *Escherichia coli* plasmid (pBR322, pBR325, pUC118 and pUC119), *Bacillus subtilis* plasmid (pUB110 and pTP5) and yeast plasmid (YEp13, YEp24 and YCp50); animal viruses, such as retrovirus, adenovirus, herpes virus, avipox virus and vaccinia virus; and binary vectors, such pPZP vectors, pGA vectors and pCAMBIA vectors.

The plasmid transfers a DNA directly to a human cell using a gene transfer technology, approved by the FDA (Nabel, E. G., et al., *Science*, 249: 1285-1288, 1990). The advantage of the plasmid over the virus vector is that it can be uniformly purified. Of the virus vectors, retrovirus is produced in a cell in which non-virus proteins are infected by a virus vector due to the removal or alteration of all virus genes. Major advantages of retrovirus for gene therapy are that it can transfer a large amount of genes into a cloned cell, precisely integrate a gene transferred into a cell DNA, and prevent gene transfection from causing repeated infection (Miller, A. D., *Nature*, 1992, 357: 455-460). Adenovirus is a type of non-retrovirus and, as major advantages, can transfer a large amount of DNA fragments (36 kb genome) and infect non-cloned cells at a very high titer (Rosenfeld, M. A., et al., *Cell*, 68: 143-155, 1992; Jaffe, H. A. et al., *Nature Genetics*, 1: 372-378, 1992; Lemarchand, P. et al., *Proc. Natl. Acad. Sci. USA*, 89: 6482-6486, 1992). Furthermore, herpes virus can also be availably used for human gene therapy (Wolfe, J. H., et al., *Nature Genetics*, 1: 379-384, 1992). It will be apparent to those skilled in the art that the present invention can adopt any vectors, which can introduce the promoter of the present invention and a base sequence for encoding a desired protein operably linked to the promoter, into a host cell.

Examples of the desired protein, which can be used in the present invention, may include any extraneous proteins, which are supposed to be oviduct-specifically expressed by the promoter of the present invention, such as an exogenous protein, an endogenous protein and a reporter protein. The exogenous protein indicates a protein that is not naturally present in a specific tissue or cell, and the endogenous protein indicates a protein that is expressed by a gene, which is naturally present in a specific tissue or cell. The reporter protein indicates a marker protein that is expressed by a reporter gene, and the presence of the reporter protein represents the activity of the reporter gene inside a cell.

According to an example of the present invention, there was produced a pGL3/AGR2/887 bp promoter vector as the above-mentioned recombinant expression vector. In the pGL3/AGR2/887 bp promoter vector, a promoter having 1996 to 2882 base sequences ($-7^{th}$ to $-893^{rd}$ from the transcription initiation site of the AGR2 gene) of SEQ ID NO: 1 was operably linking to pGL3 including a luciferase gene as a reporter gene, in a region of pGL3 upstream of the luciferase gene. As the above-mentioned recombinant expression vector, there were also produced a pGL3/AGR2/1692 bp promoter vector and a pGL3/AGR2/2882 bp promoter vector. In the pGL3/AGR2/1692 bp promoter vector, a promoter having 1191 to 2882 base sequences ($-7^{th}$ to $-1698^{th}$ from the transcription initiation site of the AGR2 gene) of SEQ ID NO: 1 was operably linked to pGL3 including a luciferase gene, in a region of pGL3 upstream of the luciferase gene. In the pGL3/AGR2/2882 bp promoter vector, a promoter having 1 to 2882 base sequences ($-7^{th}$ to $-2888^{th}$ from the transcription initiation site of the AGR2 gene) of SEQ ID NO: 1 was operably linked to pGL3 including a luciferase gene, in a region of pGL3 upstream of the luciferase gene.

The recombinant expression vector of the present invention including a promoter of the present invention and a base sequence for encoding a desired protein operably linked to the promoter can be introduced into a host cell via various methods. The host cell may be a eukaryotic cell or a prokaryotic cell, preferably, an animal cell, and more preferably, a HeLa cell.

The methods of introducing the recombinant expression vector of the present invention into the host cell may include but not limited to transient transfection, microinjection, transduction, cell fusion, calcium phosphate precipitation, liposome-mediated transfection, DEAE Dextran-mediated transfection, polybrene-mediated transfection, electroporation, gene gun technology, and other known methods of introducing a DNA into a cell (Wu et al., *J. Bio. Chem.*, 267: 963-967, 1992; Wu and Wu, *J. Bio. Chem.*, 263: 14621-14624, 1988). Preferably, the liposome-mediated transfection can be used.

Accordingly, the present invention provides a cell transformed with the above-mentioned recombinant expression vector.

The present invention also provides a method of producing a desired protein, the method including a step of culturing the above-mentioned transformed cell.

According to the method of producing a desired protein from the above-mentioned transformed cell includes procedures of: producing a recombinant expression vector by inserting a promoter of the present invention and a base sequence for encoding a desired protein operably linked to the promoter, into a suitable expression vector; and culturing a cell transformed with the recombinant expression vector so that the desired protein derived by the promoter of the present invention is expressed in the transformed cell. The method of culturing the transformed cell to express the desired protein is well-known in the art. For example, the expression of the desirable protein can be derived inoculating the transformed cell into a suitable culture medium, for species propagation, and inoculating the cell, cultured through the species propagation, into a main culture medium. When the cell is completely cultured, a desired recombinant protein, which is substantially pure, can be recovered from the cultured cell. As defined herein, the term "substantially pure" indicates that the desired protein of the present invention or a polynucleotide sequence for encoding the desired protein contains substantially no protein derived from another host cell.

The desired protein, expressed in the transformed cell, can be recovered via various methods, such as isolation and purification, as well known in the art. Generally, in order to remove cell debris and the like, the medium containing the cell can be centrifuged, followed by precipitation such as salting-out (e.g., ammonium sulfate precipitation, sodium phosphate precipitation and the like) and solvent precipitation (e.g., protein fraction precipitation using acetone, ethanol and the like), or the like. Dialysis, electrophoresis or various types of column chromatographies can also be performed. The column chromatographies may include, for example, ion exchange chromatograph, gel-permeation chromatography, high performance liquid chromatography (HPLC), reverse-phase HPLC and affinity column chromatography, ultra filtration, which can be performed alone or in combination (Maniatis et al., *Molecular Cloning: A Laboratory Manual*, Cold Spring Harbor Laboratory, Cold Spring Harbor, N.Y. (1982); Sambrook et al., *Molecular Cloning: A Laboratory Manual*, 2d Ed., Cold Spring Harbor Laboratory Press (1989); Deutscher, M., *Guide to Protein Purification Methods Enzymology*, Vol. 182. Academic Press Inc., San Diego, Calif. (1990)).

Advantageous Effects

As set forth above, the oviduct specific promoter of the invention and the recombinant expression vector of the invention including the promoter can induce the expression of a protein specifically in the oviduct, i.e., an organ that secrets proteins so as to accumulate with a large amount in the egg. Accordingly, the oviduct specific promoter and the recombinant expression vector of the present invention can be advantageously used to produce transformed chickens, which can massively yield useful elements of high added value, produce functional eggs, and improve the economic traits of the poultry.

BEST MODE

Figure 1:
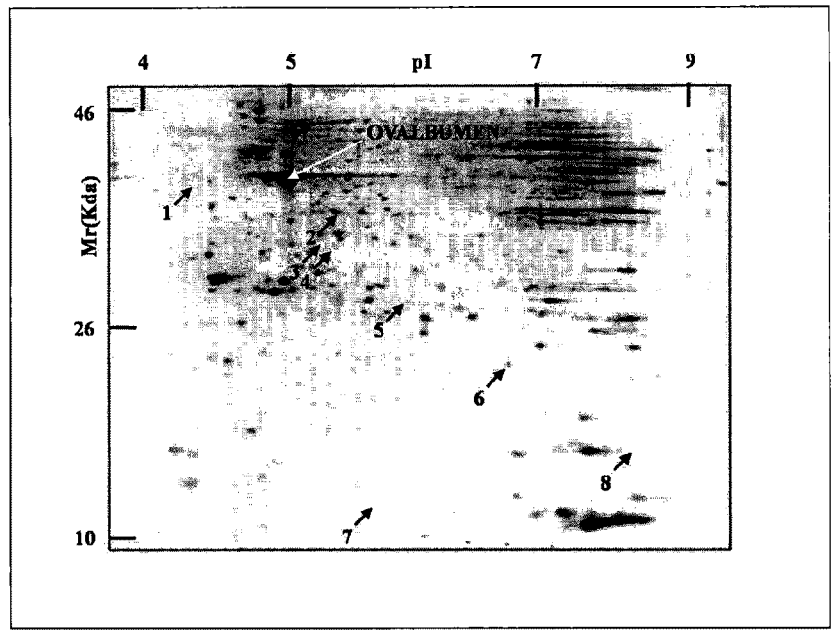
FIG. 1 is an image analysis of proteins expressed in the oviduct of a five (5) week old chicken, silver stained after second dimensional electrophoresis.

Hereinafter, the present invention will be described more fully with respect to the following examples.

However, the following examples are for the illustrative purposes only and are not to be perceived as limiting the scope of the present invention.

Example 1

Analysis of Protein Expressed in Oviduct Via Proteome Method

Experiment was performed in order to find proteins, which are expressed specifically in the oviduct tissue. That is, chicken oviducts were collected according to respective growth stages of chickens. Using proteome method, proteins were extracted and identified, which were expressed specifically in the oviduct of a thirty-five (35) week old chicken, the function of the oviduct at this age being most vigorous. Details of this process are described as follows:

1-1. Extraction of Protein from Oviduct Tissue

In order to analyze proteins expressed in the oviduct tissues, chickens (5, 35 and 65 week old chickens) were supplied from the Institute of Animal Science. First, each oviduct tissue was cut out, was mixed with a solution buffer (7M urea, 2.8M thiol urea and 4% CHAPS(3-[(3-Cholamidopropyl)-Dimethylammonio]-1-Propane Sulfonate), was homogenized using a rotor blade homogenizer, and then was brought to reaction for about one (1) hour at room temperature, in a state where the solution buffer was maintained. Then, the tissue extraction was centrifuged at 4,000rpm for 10 mins, and the upper layer liquid was moved into a new tube, followed by centrifugation at 15,000 rpm for 30 mins. The resultant upper layer liquid was moved into a new tube to be stored. Proteins in the oviduct tissue, extracted as above, were measured via Bradford assay, and then were stored at −80° C. before 2-De analysis.

1-2. First Dimensional Electrophoresis (IEF)

80 mM DTT and 0.5% IPG buffer were added to 100 μg protein, which were extracted from the oviduct of the respective week old chicken as in Example 1-1, and a rehydration solution (7M urea, 2.8M thiol urea, 4% CHAPS(3-[(3-Cholamidopropyl)-Dimethylammonio]-i-Propane Sulfonate), and 0.002% (w/v) bromophenol blue) was added, so that the entire volume of the tissue became 340 ml. Then, the resultant solution was loaded on a clean holder, and was dehydrated for 12 hours using an IPG strip (pH 3 to 10), available from Amersham Biosciences, Sweden. Next, the resultant solution was developed for 1 hour at 500V concentration gradient, and was developed for 1 hour again at 8,000V concentration gradient. Finally, isoelectrofocusing (IEF) was performed on the resultant solution for 13 hours at 8,000V steady-n-state level, so that respective proteins were separated according to each isoelectric point (pI).

1-3. Second Dimensional Electrophoresis

After the first dimensional electrophoresis was finished as mentioned above in 1-2, IPG strips of respective week old chickens were mixed with an equilibration buffer (50 mM Tris-hydrochloric acid pH 8.8, 6M urea, 30% glycerol, 2% SDS, 0.001% bromophenol blue), to which 1% DTT and 2.5% iodoacetamide (IAA) were added, and the resultant products were brought to reaction for 15 mins at room temperature. Thereafter, each strip equilibrated with the equilibration buffer was placed on a previously prepared 12% SDS-PAGE, an Agarose sealing solution was filled between the SDS-PAGE and the strip, and electrophoresis was performed at 2 watt intensity per every SDS-PAGE film. After the electrophoresis, the SDS-PAGE was brought to reaction in a fixing solution (10% acetic acid, 40% ethanol) for about 30 mins.

1-4. Silver Staining and Image Analysis

After the second dimensional electrophoresis was finished as mentioned above in Example 1-3, silver staining was performed on the SDS-PAGE gel, which was fixed with the fixing solution through, to observe the expression pattern of proteins expressed in the oviduct of respective chicken. First, the SDS-PAGE gel obtained through Example 1-3 was brought to reaction with a sensitizing solution (30% ethanol, 0.125% (w/w) glutaraldehyde, 0.2% (w/v) sodium thiol sulfate, 6.8% sodium acetate) for 30 mins, followed by cleaning with distilled water. Then, the resultant SDS-PAGE gel was brought to reaction with 0.25% (w/v) silver nitrate solution for 20 mins, followed by cleaning with distilled water. Next, the SDS-PAGE gel was brought to reaction in a developing agent (2.5% (w/v) sodium carbonate) for 8 mins, and brought to reaction with a stop solution (1.46% (w/v) EDTA.Na.2H$_2$O) to stop the staining. The SDS-PAGE gel, stained as above, was scanned using Image Scanner-Flatbed scanner (available from Amersham Biosciences, Sweden). The respective stained protein was analyzed using ImageMaster 2D Melanie software (available from Amersham Biosciences, Sweden).

Figure 2:
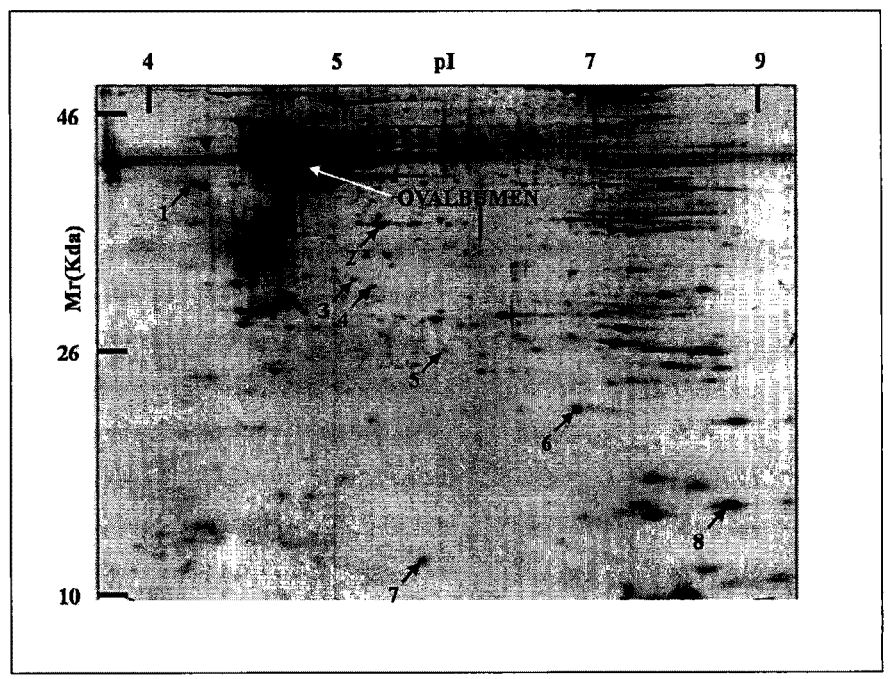
FIG. 2 is an image analysis of proteins expressed in the oviduct of a thirty-five (35) week old chicken, silver stained after second dimensional electrophoresis.
Figure 3:
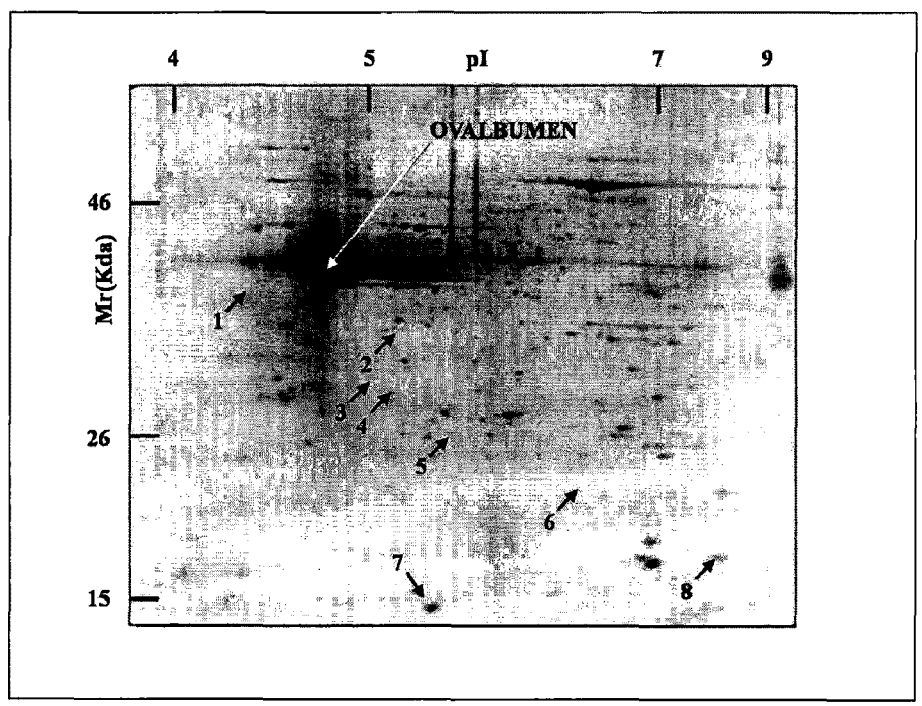
FIG. 3 is an image analysis of proteins expressed in the oviduct of a sixty-five (65) week old chicken, silver stained after second dimensional electrophoresis.

As a result, when the same amount of proteins extracted from the respective oviduct of the chickens of different growth stages, it was observed that a greatest amount of ovalbumin and other proteins were expressed in the oviduct of the 35 week old chicken (see FIG. 2). On the contrary, in the premature oviduct of the 5 week old chicken in the early growth stage or the old oviduct of the 65 week old chicken, a much less amount of ovalbumin and other proteins were expressed (see FIGS. 1 and 3). Furthermore, the image analysis proved that about 20 proteins were expressed differently according to the ages. Particularly, the 35 week old chicken had about 8 proteins, which were more highly expressed, than the 65 week old chicken. Eight (8) arrows in FIGS. 1 to 3 indicate the proteins, which were expressed at a significantly high value in the 35 week old chicken.

Example 2

Identification of Protein Expressed in Oviduct

Figure 4:
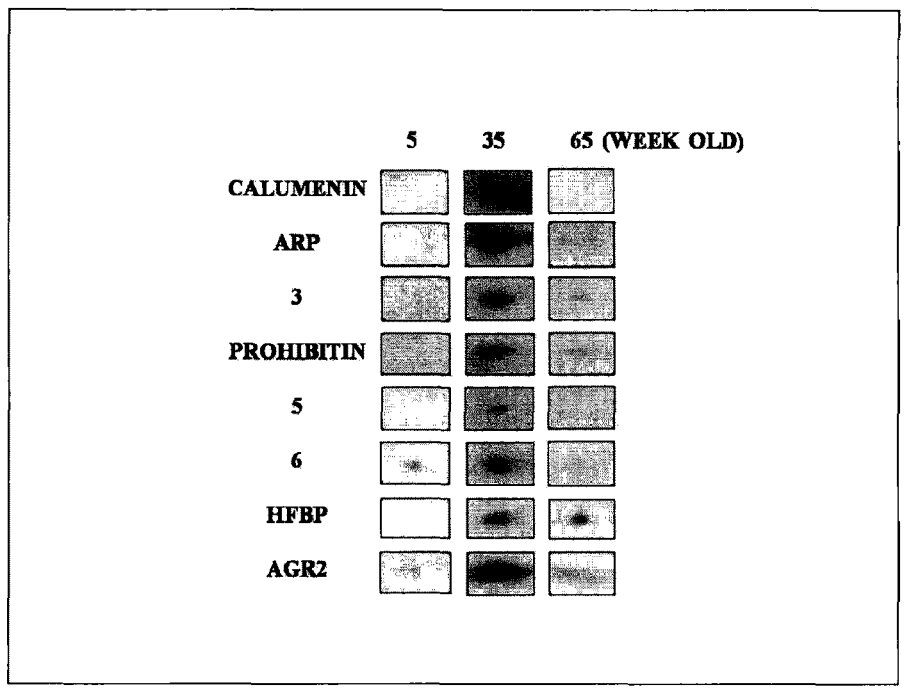
FIG. 4 is a view for comparing some proteins, which are significantly highly expressed in the oviduct of the 35 week old chicken, with the results of the 5 and 65 week old chickens.

According to the result of the image analysis of Example 1-4 above, eight (8) proteins, which were significantly highly expressed in the oviduct of the 35 week old chicken than in the oviduct of the 65 week old chicken, were identified. That is, 8 protein spots, showing a difference in expression pattern, were selected via the image analysis, and were separated respectively from the SDS-PAGE gel using a blue tip. For destaining, the separated spots were immersed into a solution with 30 mM (Potassium ferricyanide) and 100 mM sodium thiol sulfate mixed 1:1 ratio. The destained spots were pretreated using a 100 mM ammonium bicarbonate solution (pH 7.8) and an acetonitrile solution, and were brought to reaction with Trypsin to decompose the proteins. Then, protein fragments treated with Trypsin were identified using a mass spectrometer (ESI-Q-TOF, Voyager-DETM STR Biospectrometry workstation model), and the list of the identified proteins is reported in Table 1 below. The degree of expression of the 8 proteins according to the age is illustrated in FIG. 4.

TABLE 1

| No. | Protein | Genebank No. | pI | Molecular weight (kDa) |
|---|---|---|---|---|
| 1 | Calumenin | AAB97725 | 4.47 | 37.164 |
| 2 | ARP | NP_990318 | 5.72 | 34.435 |
| 3 | Not identified | | | |
| 4 | Prohibitin | AAH54971 | 5.28 | 29.859 |
| 5 | Not identified | | | |
| 6 | Not identified | | | |
| 7 | HFBP | NP_0010260660 | 5.92 | 14.807 |
| 8 | AGR2 | XP_418698 | 8.94 | 19.943 |

Note)
pI is short isoelectric point.

As reported in Table 1 above, of the 8 proteins strongly expressed only in the oviduct of the 35 week old chicken, five (5) proteins were identified, which include calumenin, also known as calcium binding protein (Genebank Accession No. AAB97725), ARP also known as estradiol independent house keeping gene (Genebank Accession No. NP_990318), prohibitin (Genebank Accession No. AAH54971), HFBP (Genebank Accession No. NP_0010260660) and AGR2 (Genebank Accession No. XP_418698); the other three proteins were not identified. Particularly, of the identified five proteins, ARP and AGR2 were expressed specifically in the 35 week old oviduct at a very high value but rarely expressed in the 5 or 65 week old oviduct; calumenin, prohibitin and HFBP were rarely expressed in the 5 or 65 week old oviduct but were weakly expressed in the 35 week old oviduct (see FIG. 4). In consideration of the results, the present inventors were able to convince that the ARP and AGR2 proteins were expressed specifically in the oviduct of the 35 week old chicken.

Example 3

Analysis of RNA Expression Status of Oviduct Specific Protein

Figure 5:
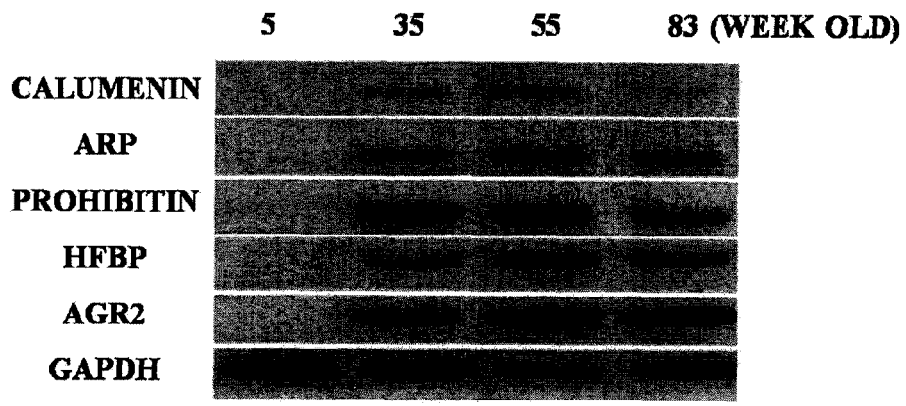
FIG. 5 is a view for comparing RNA expression of calumenin, ARP, prohibitin, HFBP and AGR2 according to the age of chickens, in which RNA was extracted from the oviduct of 5, 35, 55 and 83 week old chickens, followed by RT-PCR, GAPDH being a control group for quantity analysis.

In order to examine whether or not the five proteins, identified in Example 2 above, were expressed specifically only in the oviduct of the 35 week old chicken, RNA was extracted from the oviduct of respective 5, 35, 55 and 83 week old chickens, and RNA expression status was examined using an RT-PCR. For this purpose, entire RNA was extracted from 300 mg of duct tissue of the respective chicken using trizol reagent (available from Invitrogen, USA). That is, the oviduct tissue was dissolved by adding trizol reagent thereto, and was left alone for 10 mins at room temperature. Then, 200 μl of chloroform was added to the resultant product, followed by centrifugation with 12,000 g for 15 mins at 4° C., thereby producing an upper layer liquid. The upper layer liquid was added with the same amount of isopropanol, and was left alone for 10 mins at room temperature. The resultant product was centrifuged again with 12,000 g for 15 mins at 4° C., thereby removing the solution, so that only pellets were left. The pellets were dried at room temperature, and were dissolved into distilled water, treated with 50 μl of lease inhibitor such as DEPC, thereby acquiring RNA. Then, in order to perform a reverse transcription reaction using above-acquired RNA as a template, RNA (1 μg) of each age acquired as above, a random primer and M-MLA reverse transcriptase (available from Promega, USA) were added, and were brought to reaction at 42° C. for 1 hour, thereby acquiring cDNA of each age. Thereafter, in order to amplify the gene for encoding each of the 5 proteins as identified in Example 2 above, primers as listed in Table 2 below were prepared using the gene sequences of the identified proteins, disclosed in Genebank, and a PCR was performed using above-acquired cDNA as the template. Here, GAPDH was used as a control group for quantity analysis. The PCR was performed by a reaction at 94° C. for 5 mins, followed by a repetition of thirty (30) cycles, each cycle including reactions performed at 94° C. for 2 mins, at 55° C. for 1 min, and at 72° C. for 5 mins. Next, the last reaction was performed at 72° C. for 10 mins, and then the PCR reactant was identified via electrophoresis. The results are illustrated in FIG. 5.

TABLE 2

Primer sequence

| Desired gene | Primer sequence | | Seq. No. |
|---|---|---|---|
| Calu-menin | (F) | 5'-cac ccc gag gag tac gac ta-3' | 2 |
| | (R) | 5'-tat ttg gcc acg atc tcc tc-3' | 3 |
| ARP | (F) | 5'-tca tga aaa tca tcc aac tg-3' | 4 |
| | (R) | 5'-gat gtt cag cat gtt cag ca-3' | 5 |
| Prohi-bitin | (F) | 5'-ctc gcc cac gta aca tac ct-3' | 6 |
| | (R) | 5'-gaa ttc ctt gcc aaa ggt ca-3' | 7 |
| HFBP | (F) | 5'-atg gtg gaa gcg ttc gtg gg-3' | 8 |
| | (R) | 5'-cta tga tgc ctt ctc aga gg-3' | 9 |
| AGR2 | (F) | 5'-gcc aag cac tca aga agg tc-3' | 10 |
| | (R) | 5'-tgc tgc cct gta cag aag tg-3' | 11 |
| GAPDH | (F) | 5'-atg gtg aaa gtc gga gtc aa-3' | 12 |
| | (R) | 5'-agt gtc cgt gtg tag aat ca-3' | 13 |

Accordingly, as shown in FIG. 5, the 5 proteins identified in Example 2 above were rarely expressed in the premature 5 week old oviduct; calumenin and ARP were expressed from the 35 week old oviduct but only with a small amount. In the case of prohibitin and HFBP, high RNA expression was observed in the 35 and 55 week old oviducts, but the amount of RNA expression decreased in the 83 week old oviduct. The RNA of AGR2 was expressed very highly through the 35, 55 and 83 week old oviducts. Particularly, the RNA was expressed highly in the old oviduct of the 83 week old chicken. Even though the results are different from the above-mentioned protein expression, it is assumed that this difference was caused by post-translation modification. However, since the RNA of AGR2 was highly expressed in the 35 week old chicken, which was in the egg-laying period, it is appreciated that the AGR2 gene and the promoter thereof can be utilized as useful genes to produce functional eggs.

Example 4

Analysis of Expression Status of Oviduct Specific Protein According to Tissue In order to examine whether or not the five proteins, identified in Example 2 above, were expressed specifically only in the oviduct of the 35 week old chicken, entire RNA was extracted from certain tissues of the 35 week old chicken, such as the heart, the liver, the kidney and the muscle, in addition to the ampulla and the isthmus corresponding to the chicken oviduct, as described in Example 3 above. The expression status of RNA was examined using an RT-PCR, and the results are illustrated in FIG. 6.

Figure 6:
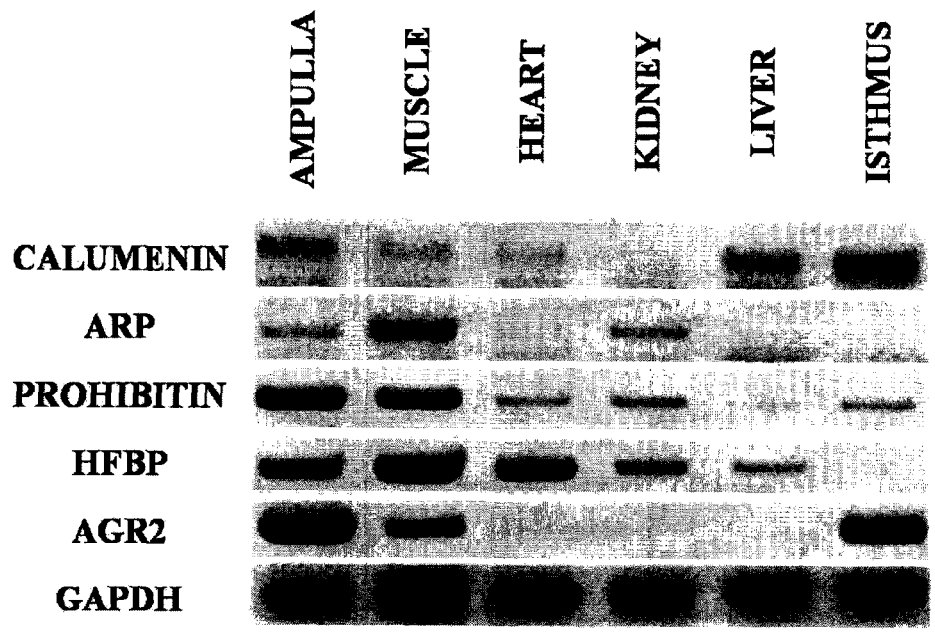
FIG. 6 is a view for comparing RNA expression of calumenin, ARP, prohibitin, HFBP and AGR2 in tissues of a chicken, in which RNA was extracted from the ampulla, the isthmus, the muscle, the heart, kidney and the liver of the chicken, followed by RT-PCT, GAPDH being a control group for quantity analysis.

As shown in FIG. 6, of the identified 5 proteins, most of four (4) proteins were expressed with a large amount in the muscle; large amounts of prohibitin, HFPB and AGR2 were expressed in the muscle and the ampulla of the oviduct. In the isthmus of the oviduct, calumenin and prohibitin were expressed but with a very small amount. On the contrary, it was observed that AGR2 was very strongly expressed in the isthmus. Accordingly, it could be understood that AGR2 of the identified five proteins is a protein that is not expressed in other tissues rather than the muscle but is expressed specifically in the oviduct tissue.

Example 5

Analysis of AGR2 Protein Expressed in White of Egg

The present inventors found that the AGR2 protein is expressed specifically in the oviduct, which secretes a large amount of proteins to be stored in the egg, and based on this finding, examined the expression of AGR2 gene in the white of the egg in order to determine whether or not function eggs, which have useful elements are accumulated therein, can be produced using the AGR2 protein. Fresh hatching eggs were purchased from the market and were artificially incubated for 0, 6, 11, 13 and 14 days in hatching facility, respectively, and entire RNA was extracted from the white of respective hatching egg in the same process as in Example 3 above, and an RT-PCR was performed. In the incubation period, incubation temperature was maintained 37.5° C. and moisture was maintained uniformly (60 to 70%) in the hatching facility, in which an automatic temperature controller was provided, and the eggs were rolled at every sixth hour. In the RT-PCR, 28S gene of the chicken (Genebank Accession No. DQ018756) was used as a control group for quantity analysis. As primers used for the RT-PCR, primers of sequence Nos. 10 and 11 were used in order to identify AGR2, and primers of sequence Nos. 14 and 15 were used in order to identify 28s of the chicken used as the control group. The RT-PCR was performed by a reaction at 95° C. for 2 mins, followed by a repetition of thirty (30) cycles, each cycle including reactions performed at 95° C. for 1 min, at 60° C. for 1 min, and at 72° C. for 1 mins, and then the PCR reactant was identified via electrophoresis. The results are illustrated in FIG. 7.

```
Sequence No. 14 primer (chicken 28s forward)
5'-ttcacgccctcttgaactct-3'

Sequence No. 15 primer (chicken 28s reverse)
5'-gcccaagtccttctgatc-3'
```

Figure 7:
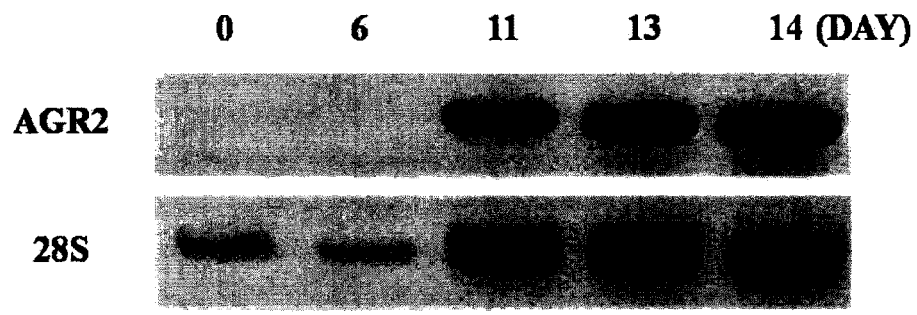
FIG. 7 is a view for comparing RNA expression of AGR2 in respective culturing stages of fresh hatching eggs, in which RNA was extracted from the white of the hatching eggs cultivated for 0, 11, 13 and 14 days, followed by RT-PCR, 28S gene being a control group for quantity analysis.

As shown in FIG. 7, it was observed that the AGR2 protein was rarely expressed in the white of the egg, which was incubated for 0 or 6 days. However, the AGR2 protein was expressed with a large amount in the white of the egg, which was incubated for 11, 13 or 14 days. According to the results, it is appreciated that the AGR2 protein is expressed specifically in the oviduct of the chicken and also is expressed in the white of the egg. Based on this finding, the present inventors assumed that the AGR2 protein can be involved in the course of forming the white of the egg, and if the promoter region of the AGR2 gene was located, it could be possible to secrete or accumulate certain useful elements in the white of the egg using the promoter region.

Example 6

Locating Promoter Region Involved in Expression of AGR2 Gene

In order to locate the promoter region of the AGR2 protein, which is expressed specifically only in the oviduct, the present inventors assumed the promoter region of the AGR2 protein to be a region corresponding to −893 bp, −1698 bp or −2888 bp upstream of a region, corresponding to −7 from the transcription initiation site (i.e., A base of ATG) of the AGR2 gene, using NCBI database. Thereafter, in order to acquire promoter DNA of the assumed AGR2 protein, the primers as presented in Table 3 below were prepared using the entire genome DNA template (Novagen) of the chicken and AGR2 (Genebank Accession No. XP_418698), and thereby a PCR was performed. The PCR was performed by a reaction at 95° C. for 2 mins, followed by a repetition of thirty (30) cycles, each cycle including reactions performed at 95° C. for 1 min, at 60° C. for 1 min, and at 72° C. for 2 mins. Acquired DNA was identified by Agarose gel electrophoresis, the resultant PCR products were cloned using pGEN-T Easy vector (Promega, USA) in order to clone base sequences of the PCR product, and the analysis of the base sequences was entrusted to Bionics.

TABLE 3

AGR2 primer sequence

| Primer | Base sequence | Seq. No. |
| --- | --- | --- |
| AGR2 forward promoter (−7 to −2888) | 5'-GG GGTACC AGAAACTGCATGGATGTG-3' | 16 |
| AGR2 backward promoter | 5'-CC CTCGAG CCCTGAAATGAAGAAGAG-3' | 17 |
| AGR2 forward promoter (−7 ~ −1698) | 5'-GG GGTACC TGCTTTGGTAGGGGAAAG-3' | 18 |
| AGR2 backward promoter | 5'-CC CTCGAG CCCTGAAATGAAGAAGAG-3' | 17 |
| AGR2 forward promoter (−7 ~ −893) | 5'-GG GGTACC CATTTTCATTGTCTGAAT-3' | 19 |
| AGR2 backward promoter | 5'-CC CTCGAG CCCTGAAATGAAGAAGAG-3' | 17 |

Figure 8:
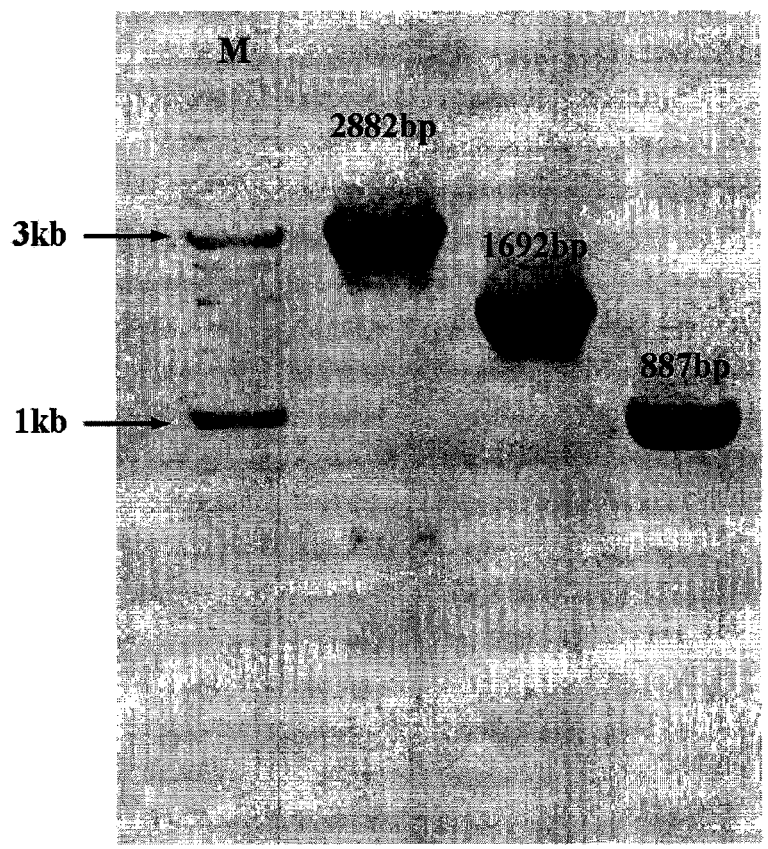
FIG. 8 illustrates the results produced by performing PCR on some regions of AGR2 gene, which correspond to −893 bp, −1698 bp and −2888 bp upstream of −7 from the transcription initiation site of the AGR2 gene, assumed as a promoter region thereof, using the genome DNA of a chicken as a template, followed by Agarose gel electrophoresis.

As shown in FIG. 8, the region corresponding to −893 bp, −1698 bp or −2888 bp upstream of the region, corresponding to −7 from the transcription initiation site of the AGR2 gene, assumed as the promoter region of the AGR2 protein, was identified by Agarose gel electrophoresis. Furthermore, the base sequence including −2888 bp upstream of the region, corresponding to −7 from the transcription initiation site of the AGR2 gene was represented with SEQ ID NO: 1.

Example 7

Figure 9:
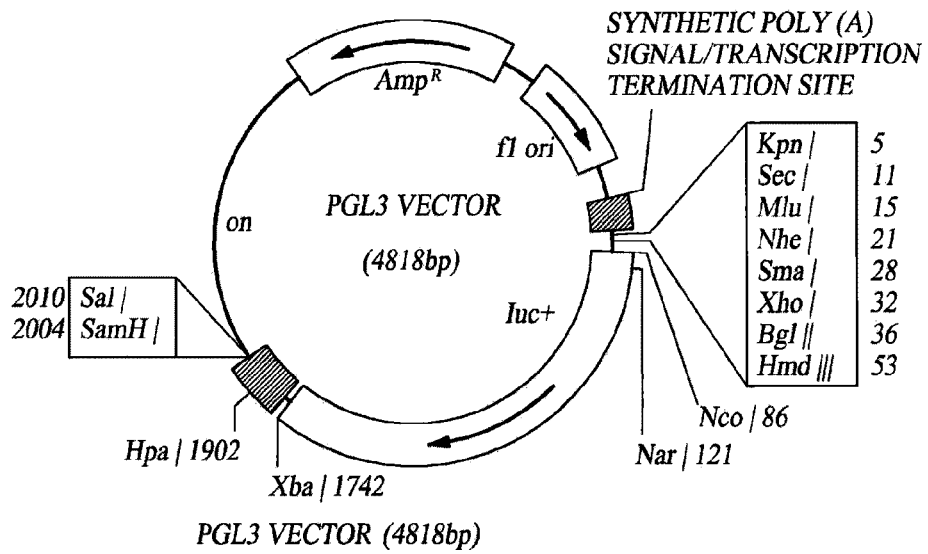
FIG. 9 illustrates a map of a recombinant vector of the present invention produced by operably linking base sequences of AGR2 gene, which correspond to −893 bp, −1698 bp and −2888 bp upstream of −7 from the transcription initiation site of the AGR2 gene, assumed as a promoter region thereof, to a pGL3 vector including a luciferase gene as a reporter gene.
Figure 9:
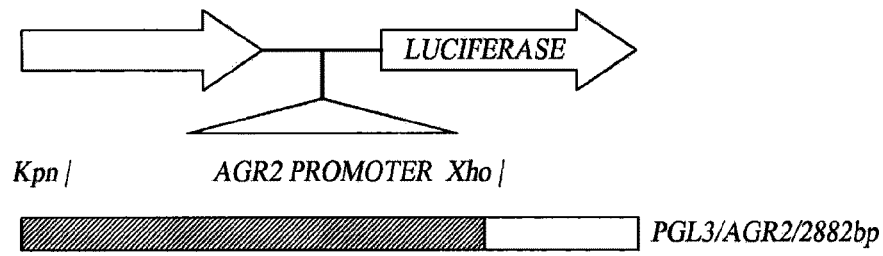
Figure 9:
Figure 9:
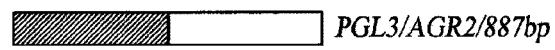

Examining Activity of AGR2 Promoter 7-1. Production of Recombinant Vector Including Promoter of AGR2 Gene In order to examine promoter activity of the region assumed as the promoter of the AGR2 protein, acquired through the PCR in Example 6 above, a recombinant expression vector including a gene corresponding to −893 bp, −1698 bp or −2888 bp upstream of the region, corresponding to −7 from the transcription initiation site of the AGR2 gene, was produced. That is, the PCR products acquired in Example 6 above were cut using restriction enzymes such as KpnI and XhoI, and then were inserted into pGL3 vector, cut via the same restriction enzymes. Here, a base sequence for encoding a luciferase protein was operably linked to the pGL3 vector, downstream of the base sequence of the inserted promoter region of the present invention. Accordingly, the inventors produced recombinant vectors, such as pGL3/AGR2/887 bp promoter vector, pGL3/AGR2/1692 bp promoter vector and pGL3/AGR2/2882 bp promoter vector, each of which includes the base sequence of −893 bp, −1698 bp or −2888 bp upstream of the region, corresponding to −7 from the transcription initiation site of the AGR2 gene. The map of the produced recombinant vectors is illustrated in FIG. 9.

7-2. Measuring Promoter Activity

The recombinant vector, produced in Example 7-1 above, was transformed into a HeLa cell of the human, and the activity of the AGR2 promoter in the HeLa cell was measured. That is, using 3 µg of the recombinant vector produced as above, 20 µl of Lipofectamine reagent (ExGen) and 1 µg of Lac Z vector (Invitrogen, USA), Hela cells (ATTC, USA) cultured under conditions of 37° C. and 5% $CO_2$ in a DMEM medium containing 10% calf bovine serum (CBS) were treated to transform. Here, a vector having no promoter inserted thereinto was used as a control group. After 28 hours passed, transformed cells were acquired via centrifugation, and were dissolved using a solution buffer (125 mM Tris solution (pH 7.8, controlled with $H_3PO_4$), 10 mM EDTA, 10 mM DTT, 50% glycerol and 5% Triton X-100). 20 µl of the dissolved cell solution and 100 µl of a buffer including beetle luciferin were mixed with each other to have reaction. The resultant product was measured using a luminometer (TURNER Biosyste) according to a measuring method disclosed by the provider, and the effect of transformation was standardized using the Lac Z vector. That is, 100 µl of the dissolved cell solution including the Lac Z vector was mixed with 500 µl of Z buffer ($Na_2HPO_4 \cdot 7H_2O$, $NaH_2PO_4 \cdot H0O$, 1M potassium chloride, 1M magnesium sulfate, pH 6.95) having 1.35 µl of betamercaptoethanol (BME) and 50 µl of 10×ONPG (1M $Na_2HPO_4$, 1M $NaH_2PO_4$, ONOG) added thereto. The mixture was brought to reaction at 28° C. for 10 mins, and when the cell solution was yellow, color reaction was stopped by adding 250 µl of 1M $Na_2CO_3$ to the mixture. Thereafter, absorbance at 420 nm was measured. The measurement of the activity of the promoter as above was repeated three times, and the results are illustrated in FIG. 10.

Figure 10:
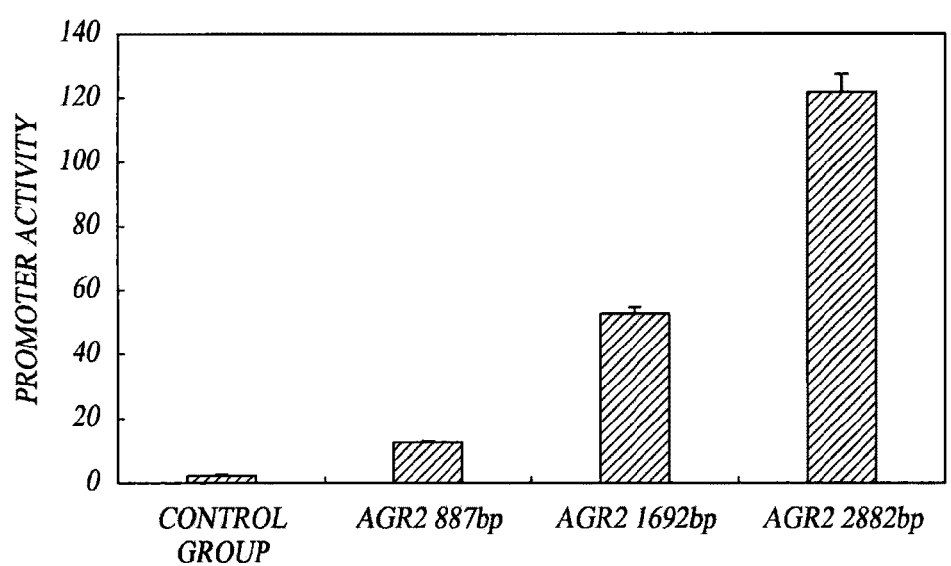
FIG. 10 illustrates the activity of a promoter having base sequences, which correspond to −893 bp, −1698 bp and −2888 bp upstream of −7 from the transcription initiation site of AGR2 gene, analyzed via luciferase assy.

As shown in FIG. 10, it can be observed that the promoter having any of base sequences −893 bp, −1698 bp and −2888 bp upstream of the region, which corresponds to −7 from the transcription initiation site of the AGR2 gene, has significantly higher activity than the control group. Particularly, the activity of the promoter having base sequences −7 to −2888 bp from the transcription initiation site of the AGR2 gene increased about eight (8) times compared to that of the promoter having base sequences −7 to −893 bp from the transcription initiation site of the AGR2 gene, and the activity of the promoter having base sequences −7 to −1698 bp from the transcription initiation site of the AGR2 gene increased about 3.5 times compared to that of the promoter having base sequences −7 to −893 bp from the transcription initiation site of the AGR2 gene. In view of the results, it was convinced that the base sequences −7 to −893 bp, −7 to −1698 bp and −7 to −2888 bp from the transcription initiation site of the AGR2 gene were the promoter regions expressed specifically in the oviduct.

The invention claimed is:

1. An oviduct specific expression promoter comprising the nucleotide sequence of residue 1996 to residue 2882 of SEQ ID NO: 1.

2. The oviduct specific expression promoter according to claim 1, comprising the nucleotide sequence of residue 1191 to residue 2882 of SEQ ID NO: 1.

3. The oviduct specific expression promoter according to claim 1, comprising the nucleotide sequence of residue 1 to residue 2882 of SEQ ID NO: 1.

4. A recombinant expression vector comprising the promoter of claim 1, and a nucleotide sequence encoding a desired protein operably linked to the promoter.

5. The recombinant expression vector according to claim 4, comprising a pGL3/AGR2/887 bp promoter vector, a pGL3/AGR2/1692 bp promoter vector, or a pGL3/AGR2/2882 bp promoter vector.

6. A cell transformed with the recombinant expression vector of claim 4.

7. A method of producing a desired protein, the method comprising culturing the cell of claim 6.

8. A recombinant expression vector comprising the promoter of claim 2, and a nucleotide sequence encoding a desired protein operably linked to the promoter.

9. The recombinant expression vector according to claim 8, comprising a pGL3/AGR2/1692 bp promoter vector or a pGL3/AGR2/2882 bp promoter vector.

10. A cell transformed with the recombinant expression vector of claim 8.

11. A method of producing a desired protein, the method comprising culturing the cell of claim 10.

12. A recombinant expression vector comprising the promoter of claim 3, and a nucleotide sequence encoding a desired protein operably linked to the promoter.

13. The recombinant expression vector according to claim 12, comprising a pGL3/AGR2/2882 bp promoter vector.

14. A cell transformed with the recombinant expression vector of claim 12.

15. A method of producing a desired protein, the method comprising culturing the cell of claim 14.

* * * * *

SEQUENCE LISTING

<160> NUMBER OF SEQ ID NOS: 19

<210> SEQ ID NO 1
<211> LENGTH: 2897
<212> TYPE: DNA
<213> ORGANISM: Gallus gallus

<400> SEQUENCE: 1

```
agaaactgca tggatgtgct ttggatacac gatactgaag ctaacaaaat acacctccag      60
ctcttcagat agaaggacca gagcagaaac atgaattcat atgctctctc tctcatttta     120
ttccttgatc agactatcga tgacataaac cacacagaaa cagacattac agtgactgac     180
ctccttggga gctggatttc acccttttca tatgtcaagc acctaaccaa agcatggtac     240
tcctgtacat gtggaagtaa aagcagctgc ttccttgctt gagttcaaca tcttgcttct     300
taccccattt tcccaatcat gctttacaaa agatttttt aagagtgatc caaagcacta      360
ttttctccta agtatattca aaaaatatgc gtgtcatgaa cagccatcag agagcactat     420
agatctcaga gagtaaatcc atatgtcgga tgggtttgac tcacccaact gagtaacact     480
cagccctcac tgtgaacctg tagttccaat cacactagaa cacaggacgc ctgcacctag     540
aacacatttt tgtttcagcc agttgtggca aagaccctct tgctgtgctg aggaaggagt     600
tgggtaggcc ctgcagcacc aagatgaaca catgggagag agctacctcg gtatacgagt     660
gtctgaaacc taaagggat ggttttcatg gtgtataagc atccacacaa ctgattaaac      720
ttggaatttg agttaaactc ttatttaagc ctcagcttat gaacacagtt tattcctgta     780
gctacaaaac acctccctgc cgagagcttt ataactgttc tcttacattt cattaaactt     840
ttcttgtgtg gtgttatttg tgcatgtaca catacatgta caatgtgcac agttaattac     900
```

```
ctaattaaca tctggagctc tgagtcacca atttaactttt ttcagaggaa taaaggaacg    960
gtgacccatg tgtgttttcc agccaatcaa aaaaagacaa atcactcctc aggcaaatca   1020
ggagtctcga cttaagctta cctggacttg gatctttgcc agcatttttta aatcactttc   1080
ctaaatgtcc taaaaagccc ccagaaacat ctctgatgtt tacagtcggt ccatagcagg   1140
aaagtgtggc attaattcat aataaaatta caacaaagt taaccctgaa tgctttggta    1200
ggggaaagat tggcaaatgc agctcttttgg gaatagtatt caaattcaaa gctcatgggt   1260
ggagacaggg agtgcaaagg tgcataaata ggcaggaggg agcgtggtgc tctcactgtg   1320
accaggaaca ccttcgcacc ccagcaggca cctggctgag cacacacggt aaggcagcac   1380
tcactcttcg gaactgccag cataacactg gggtaactgg ggctgcagca atgggaggga   1440
gaggcagtag tgtgggcaca gcacagctcc tagccataag gacacacaga gatatgttgt   1500
ccttgcaagt tacaagacac aggagagaag gggctttatg gagcagaaaa ttaagcagag   1560
gtacacacag ccttccaaag gggaagtatt caaagaggag gtttaatgtt tctgtcttgg   1620
ctttctgcac cagtaacagc gtaaactttg cctggtcttt gacttccttg ttatccaata   1680
cccttttttt ttttctcctt tcagtaagca ttacttcctc tacacagcta cagccaaaac   1740
aactcaaggc agccttgaaa atccattata tttaatgtaa atttattcaa ttttcttcct   1800
tgccaaggag acctttcttg ggacaggtag tctcctgcaa aatcctatttt catgcccttg   1860
caatccactc tgtggatgct tagaggtctc ttggacaccc agcagttaag agcattgtat   1920
cattgatgca gattcagcta atgcctcctc ctgcagttct tacccagaga aaagattccg   1980
ttttcctgga cttctcattt tcattgtctg aattttaaaa gctgtttact taaattttttg   2040
catgaatgtt ctgaattttc tggtatttca gttttaggaa taagttcaat gagaaaaaca   2100
taggctcatg ctaaagtatt ttccccttca aagcatccca gctgaaatgc tgaggagctt   2160
ccatcagtca tgccttgtct ccaccccca tgcctcagtc aggtgcagga gaagcaatct    2220
gctttgtgct gcttataatg gcaaaataca ctttggttct caccattccc cactccttct   2280
attataaaat tctactgctt ttcaggatta gatgacgcta attagagaag acaggatgta   2340
aagttccagc agcagcattg ggctatgtct atgctaacag atcactatta aacccagctt   2400
agacttctat gactcatttg agtccctctt gctgcagaag ggatgaagag cccgcatgag   2460
ttagtcaata cccatactgt taaactgcct agctacttta tcagtgggag atccagaaa    2520
aaatgggagt tcattaggac ttagaagtac ttttgaaatc aacaaaactc tgttgtttca   2580
ctgagaaaac tcaatatatg taaaatgaac aaagacaaac ttaatacagg cgtgcaactt   2640
aagcggacca caggtcctct taacgtccgc aatggcacca acacagcaga aagcagccaa   2700
accctcatg actctttgca aagcaaacct ctcccttccg ttacactccc ccgagccccc    2760
acctggagca gttagctgac tcacccagct gcatacctga ccacggcggt gcctccagct   2820
gcatctcaga accagcagca gggaggcacg gagaaatgaa ggctctcttc ttcatttcag   2880
gggcagccat ggagaag                                                 2897
```

<210> SEQ ID NO 2
<211> LENGTH: 20
<212> TYPE: DNA
<213> ORGANISM: Artificial Sequence
<220> FEATURE:
<223> OTHER INFORMATION: calumenin forward primer

<400> SEQUENCE: 2
caccccgagg agtacgacta                                                20

```
<210> SEQ ID NO 3
<211> LENGTH: 20
<212> TYPE: DNA
<213> ORGANISM: Artificial Sequence
<220> FEATURE:
<223> OTHER INFORMATION: calumenin reverse primer

<400> SEQUENCE: 3
tatttggcca cgatctcctc                                                 20

<210> SEQ ID NO 4
<211> LENGTH: 20
<212> TYPE: DNA
<213> ORGANISM: Artificial Sequence
<220> FEATURE:
<223> OTHER INFORMATION: ARP forward primer

<400> SEQUENCE: 4
tcatgaaaat catccaactg                                                 20

<210> SEQ ID NO 5
<211> LENGTH: 20
<212> TYPE: DNA
<213> ORGANISM: Artificial Sequence
<220> FEATURE:
<223> OTHER INFORMATION: ARP reverse primer

<400> SEQUENCE: 5
gatgttcagc atgttcagca                                                 20

<210> SEQ ID NO 6
<211> LENGTH: 20
<212> TYPE: DNA
<213> ORGANISM: Artificial Sequence
<220> FEATURE:
<223> OTHER INFORMATION: prohibitin forward primer

<400> SEQUENCE: 6
ctcgcccacg taacatacct                                                 20

<210> SEQ ID NO 7
<211> LENGTH: 20
<212> TYPE: DNA
<213> ORGANISM: Artificial Sequence
<220> FEATURE:
<223> OTHER INFORMATION: prohibitin reverse primer

<400> SEQUENCE: 7
gaattccttg ccaaaggtca                                                 20

<210> SEQ ID NO 8
<211> LENGTH: 20
<212> TYPE: DNA
<213> ORGANISM: Artificial Sequence
<220> FEATURE:
<223> OTHER INFORMATION: HFBP forward primer

<400> SEQUENCE: 8
atggtggaag cgttcgtggg                                                 20

<210> SEQ ID NO 9
<211> LENGTH: 20
<212> TYPE: DNA
<213> ORGANISM: Artificial Sequence
<220> FEATURE:
<223> OTHER INFORMATION: HFBP reverse primer
```

```
<400> SEQUENCE: 9
ctatgatgcc ttctcagagg                                              20

<210> SEQ ID NO 10
<211> LENGTH: 20
<212> TYPE: DNA
<213> ORGANISM: Artificial Sequence
<220> FEATURE:
<223> OTHER INFORMATION: AGR2 forward primer

<400> SEQUENCE: 10
gccaagcact caagaaggtc                                              20

<210> SEQ ID NO 11
<211> LENGTH: 20
<212> TYPE: DNA
<213> ORGANISM: Artificial Sequence
<220> FEATURE:
<223> OTHER INFORMATION: AGR2 reverse primer

<400> SEQUENCE: 11
tgctgccctg tacagaagtg                                              20

<210> SEQ ID NO 12
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 12
atggtgaaag tcggagtcaa                                              20

<210> SEQ ID NO 13
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 13
agtgtccgtg tgtagaatca                                              20

<210> SEQ ID NO 14
<211> LENGTH: 20
<212> TYPE: DNA
<213> ORGANISM: Artificial Sequence
<220> FEATURE:
<223> OTHER INFORMATION: chicken 28s forward primer

<400> SEQUENCE: 14
ttcacgccct cttgaactct                                              20

<210> SEQ ID NO 15
<211> LENGTH: 18
<212> TYPE: DNA
<213> ORGANISM: Artificial Sequence
<220> FEATURE:
<223> OTHER INFORMATION: chicken 28s reverse primer

<400> SEQUENCE: 15
gcccaagtcc ttctgatc                                                18

<210> SEQ ID NO 16
<211> LENGTH: 26
<212> TYPE: DNA
```

```
<213> ORGANISM: Artificial Sequence
<220> FEATURE:
<223> OTHER INFORMATION: AGR2(-7~-2888) forward primer

<400> SEQUENCE: 16
ggggtaccag aaactgcatg gatgtg                                     26

<210> SEQ ID NO 17
<211> LENGTH: 26
<212> TYPE: DNA
<213> ORGANISM: Artificial Sequence
<220> FEATURE:
<223> OTHER INFORMATION: AGR2 reverse primer

<400> SEQUENCE: 17
ccctcgagcc ctgaaatgaa gaagag                                     26

<210> SEQ ID NO 18
<211> LENGTH: 26
<212> TYPE: DNA
<213> ORGANISM: Artificial Sequence
<220> FEATURE:
<223> OTHER INFORMATION: AGR2(-7~-1698) forward primer

<400> SEQUENCE: 18
ggggtacctg ctttggtagg ggaaag                                     26

<210> SEQ ID NO 19
<211> LENGTH: 26
<212> TYPE: DNA
<213> ORGANISM: Artificial Sequence
<220> FEATURE:
<223> OTHER INFORMATION: AGR2(-7~-893) forward primer

<400> SEQUENCE: 19
ggggtaccca ttttcattgt ctgaat                                     26
```